United States Patent
Lee et al.

(10) Patent No.: US 11,021,429 B1
(45) Date of Patent: Jun. 1, 2021

(54) METHODS FOR PRODUCING A METHANOL PRECURSOR, METHANOL, AND A METHYL ESTER FROM METHANE IN HIGH PURITIES

(71) Applicant: KOREA INSTITUTE OF SCIENCE AND TECHNOLOGY, Seoul (KR)

(72) Inventors: Hyun Joo Lee, Seoul (KR); Ung Lee, Seoul (KR); He Won Lee, Seoul (KR); Tran Huyen Dang, Seoul (KR); Seok Hyeon Cheong, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 16/943,179

(22) Filed: Jul. 30, 2020

(30) Foreign Application Priority Data

Feb. 7, 2020 (KR) .................. 10-2020-0015074

(51) Int. Cl.
*C07C 51/64* (2006.01)
*C07C 51/493* (2006.01)
*C07C 29/88* (2006.01)

(52) U.S. Cl.
CPC .............. *C07C 51/64* (2013.01); *C07C 29/88* (2013.01); *C07C 51/493* (2013.01)

(58) Field of Classification Search
CPC ........ C07C 51/64; C07C 51/493; C07C 29/88
See application file for complete search history.

(56) References Cited

FOREIGN PATENT DOCUMENTS

| CN | 1400198 A | 3/2003 |
| CN | 101397237 A | 4/2009 |
| CN | 101633604 A | 1/2010 |

OTHER PUBLICATIONS

Zimmermann et al, Journal of the American Chemical Society, Selective Methane Oxidation Catalyzed by Platinum Salts in Oleum at Turnover Frequencies of Large-Scale Industrial Processes, 2016, 138, pp. 12395-12400. (Year: 2016).*
H.T. Dang et al., "Enhanced Catalytic Activity of (DMSO)2PtCl2 at the Methane Oxidation in SO3—H2SO4 System", ACS Catalysis, Nov. 8, 2018.
H.W. Lee et al., "Pt black catalyzed methane oxidation to methyl bisulfate in H2SO4—SO3", Journal of Catalysis, May 13, 2019, 374, 230-236.
T. Zimmermann et al., "Selective Methane Oxidation Catalyzed by Platinum Salts in Oleum at Turnover Frequencies of Large-Scale Industrial Processes", Journal of the American Chemical Society, Sep. 5, 2016.

* cited by examiner

*Primary Examiner* — Paul A Zucker
(74) *Attorney, Agent, or Firm* — Rabin & Berdo, P.C.

(57) ABSTRACT

A method for producing a methanol precursor, methyl trifluoroacetate, having high-purity includes the steps of (a) preparing methyl bisulfate by mixing a catalyst with an acid solution comprising a sulfur-containing acid to provide a first mixture and supplying methane gas to the first mixture to prepare the methyl bisulfate; and (b) preparing methyl trifluoroacetate ($CF_3CO_2CH_3$) by adding trifluoroacetic acid ($CF_3CO_2H$) to the first mixture including the methyl bisulfate to provide a second mixture and distilling the second mixture under heating to prepare, separate and purify the methyl trifluoroacetate ($CF_3CO_2CH_3$). Methanol may be produced by adding water to the methyl trifluoroacetate ($CF_3CO_2CH_3$). A methyl ester represented by Formula 2 below may be produced by adding a carboxylic acid represented by Formula 1 below to the methyl trifluoroacetate ($CF_3CO_2CH_3$):

$$R_1CO_2H \quad (1),$$

where $R_1$ is selected from $C_1$-$C_{10}$ alkyl groups, $$R_1CO_2CH_3 \quad (2),$$

where $R_1$ is as defined in Formula 1.

15 Claims, 4 Drawing Sheets

METHODS FOR PRODUCING A METHANOL PRECURSOR, METHANOL, AND A METHYL ESTER FROM METHANE IN HIGH PURITIES

CROSS-REFERENCE TO RELATED APPLICATIONS

This application claims priority under 35 U.S.C. § 119 to Korean Patent Application No. 10-2020-0015074 filed on Feb. 7, 2020 in the Korean Intellectual Property Office, the disclosure of which is incorporated herein by reference in its entirety.

BACKGROUND OF THE INVENTION

1. Field of the Invention

The present invention relates to methods for producing a methanol precursor, methanol, and a methyl ester by oxidation of methane, and more specifically to methods for producing methyl trifluoroacetate, methanol, and a methyl ester including oxidizing methane in the presence of oleum.

2. Description of the Related Art

Methane is the most abundant resource on earth and has very good chemical stability. Thus, methane is considered as an important alternative energy source to fossil fuels when its potential and economic efficiency are taken into account.

However, methane exists in gaseous form and has a low boiling point (−161.5° C.). For these reasons, methane is difficult to transport and carry, limiting its use. The conversion of methane to liquid methanol by partial oxidation would allow the use of methane as both a fuel and a raw material for chemical products while overcoming the disadvantages of methane gas. This is expected to change the paradigm of energy and resources on earth.

Methanol is currently synthesized from methane through a two-step reaction: conversion of methane to syngas (CO+ $H_2$) by reforming and conversion of the syngas to methanol. However, the conversion of methane to syngas requires a high temperature of at least 800° C., which is very energy consuming. In attempts to solve this problem, many techniques for direct oxidation of methane are being investigated.

Particularly, direct oxidation of methane with $O_2$ may cause more rapid degradation of methanol. Oxidation of methane with an oxidant such as $H_2O_2$ or $K_2S_2O_8$ has the disadvantages that the raw material is very expensive and the reaction yield is as low as 30% or less.

As solutions to the above problems, methods for synthesizing methyl bisulfate (MBS) as a methanol precursor using oleum were developed (see Reaction 1).

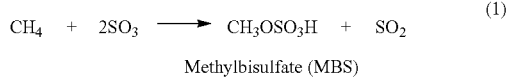

Methylbisulfate (MBS)

The oleum acts as both an oxidant and as a solvent. The methods can be carried out at low temperatures of 180 to 220° C. and have yields of 80% or more (Zimmermann, T.; Soorholtz, M.; Bilke, M.; Schüth, F. Selective Methane Oxidation Catalyzed by Platinum Salts in Oleum at Turnover Frequencies of Large-Scale Industrial Processes. J. Am. Chem. Soc. 2016, 138, 12395-12400; Hee Won Lee; Huyen Tran Dang; Honggon Kim a; Ung Lee a; Jeong-Myeong Ha a, b; Jungho Jae c; Minserk Cheong d; Hyunjoo Lee; Pt black catalyzed methane oxidation to methyl bisulfate in $H_2SO_4$—$SO_3$. Journal of Catalysis 374 (2019) 230-236; and Huyen Tran Dang; Hee Won Lee; Jieon Lee; Hyunah Choo; Soon Hyeok Hong; Minserk Cheong; and Hyunjoo Lee; Enhanced Catalytic Activity of (DMSO)2PtCl2 for the Methane Oxidation in the $SO_3$—$H_2SO_4$ System. ACS Catal. 2018, 8, 11854-11862). However, the methyl bisulfate (MBS) needs to be separated from the solvent sulfuric acid to produce the final product methanol. The hydrogen bonding between the methyl bisulfate and the sulfuric acid makes it difficult to separate them.

Processes for synthesizing desired products by oxidation of methane with $SO_3/H_2SO_4$ are known in Chinese Patent Publication Nos. 101397237, 001400198, and 101633604. However, these patent publications fail to propose specific conditions for separating methyl bisulfate from sulfuric acid and rather describe that methyl bisulfate (MBS) is converted to dimethyl sulfate ($CH_3OSO_3CH_3$) as an actual product by disproportionation during distillation.

Further, the Chinese patent publications disclose that methyl bisulfate is separated from sulfuric acid by distillation at 140° C. under high vacuum (0.1 mbar) after methane oxidation. Moreover, desired purities of the methyl bisulfate cannot be achieved because sulfuric acid, $SO_3$, and dimethyl sulfate coexist with the methyl bisulfate.

SUMMARY OF THE INVENTION

One object of the present invention is to provide a method for producing methyl trifluoroacetate in high purity.

A further object of the present invention is to provide a method for producing methanol.

Another object of the present invention is to provide a method for producing a methyl ester.

One aspect of the present invention provides a method for producing methyl trifluoroacetate, including (A) mixing a catalyst with an acid solution and supplying methane gas to the mixture to prepare methyl bisulfate and (B) adding trifluoroacetic acid ($CF_3CO_2H$) to the methyl bisulfate and distilling the mixture under heating to separate and purify methyl trifluoroacetate ($CF_3CO_2CH_3$).

The catalyst may be selected from the group consisting of Pt(0), $PtCl_2$, $PtBr_2$, $PtI_2$, Pt, $Pt(acac)_2$, $Pt(OAc)_2$, (bpym)$PtCl_2$, $(DMSO)_2PtCl_2$, NaI, KI, LiI, $CH_3I$, $CH_3CH_2I$, and $CH_3CH_2CH_2I$.

The acid may be sulfuric acid or oleum.

In step (B), the methyl bisulfate and the trifluoroacetic acid ($CF_3CO_2H$) may be mixed in a molar ratio of 1:1 to 1:10.

Step (B) may be carried out at 70 to 100° C.

A further aspect of the present invention provides a method for producing methanol, including (A) mixing a catalyst with an acid solution and supplying methane gas to the mixture to prepare methyl bisulfate, (B) adding trifluoroacetic acid ($CF_3CO_2H$) to the methyl bisulfate and distilling the mixture under heating to separate and purify methyl trifluoroacetate ($CF_3CO_2CH_3$), and (C) adding water to the methyl trifluoroacetate ($CF_3CO_2CH_3$) to produce methanol.

The catalyst may be selected from the group consisting of Pt(0), $PtCl_2$, $PtBr_2$, $PtI_2$, Pt, $Pt(acac)_2$, $Pt(OAc)_2$, (bpym)$PtCl_2$, $(DMSO)_2PtCl_2$, NaI, KI, LiI, $CH_3I$, $CH_3CH_2I$, and $CH_3CH_2CH_2I$.

The acid may be sulfuric acid or oleum.

In step (B), the methyl bisulfate and the trifluoroacetic acid ($CF_3CO_2H$) may be mixed in a molar ratio of 1:1 to 1:10.

Step (B) may be carried out at 60 to 100° C.

Another aspect of the present invention provides a method for producing a methyl ester, including (a) mixing a catalyst with an acid solution and supplying methane gas to the mixture to prepare methyl bisulfate, (b) adding trifluoroacetic acid ($CF_3CO_2H$) to the methyl bisulfate and distilling the mixture under heating to separate and purify methyl trifluoroacetate ($CF_3CO_2CH_3$), and (c) adding the methyl trifluoroacetate ($CF_3CO_2CH_3$) with a carboxylic acid represented by Formula 1:

$$R_1CO_2H \quad (1)$$

wherein $R_1$ is selected from $C_1$-$C_{10}$ alkyl groups, to produce a methyl ester represented by Formula 2:

$$R_1CO_2CH_3 \quad (2)$$

wherein $R_1$ is as defined in Formula 1.

The catalyst may be selected from the group consisting of Pt(0), $PtCl_2$, $PtBr_2$, $PtI_2$, Pt, $Pt(acac)_2$, $Pt(OAc)_2$, (bpym)$PtCl_2$, $(DMSO)_2PtCl_2$, NaI, KI, LiI, $CH_3I$, $CH_3CH_2I$, and $CH_3CH_2CH_2I$.

The acid may be sulfuric acid or oleum.

In step (B), the methyl bisulfate and the trifluoroacetic acid ($CF_3CO_2H$) may be mixed in a molar ratio of 1:1 to 1:10.

Step (B) may be carried out at 70 to 100° C.

The method for producing methanol according to the present invention can overcome the difficulties in separating and purifying the intermediate methyl bisulfate from sulfuric acid which are encountered in conventional methods for producing methanol using a platinum or iodine catalyst.

In addition, the method for producing methanol according to the present invention is advantageous over conventional methods in that high-purity methyl trifluoroacetate can be obtained as a methanol precursor that is easy to separate and purify from by-products such as sulfuric acid and high-purity methanol can be produced in a continuous manner.

Furthermore, the method for producing high-purity methanol according to the present invention involves a two-step reaction to form a methanol precursor in a simple manner without any problems and enables effective removal of by-products, particularly complete removal of sulfuric acid.

Moreover, the method for producing a methyl ester according to the present invention can continuously reuse the catalyst without discharging wastewater from sulfuric acid and methane gas to produce a high-purity methyl ester in high yield.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
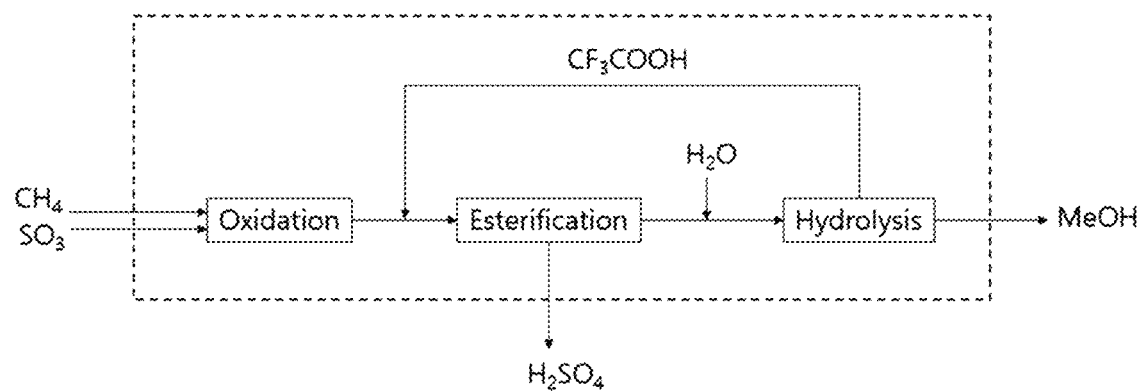
FIG. 1 schematically shows a continuous process for producing methanol by reaction of oleum with methane.

Several aspects and various embodiments of the present invention will now be described in more detail.

One aspect of the present invention is directed to a method for producing methyl trifluoroacetate, including (A) mixing a catalyst with an acid solution and supplying methane gas to the mixture to prepare methyl bisulfate and (B) adding trifluoroacetic acid ($CF_3CO_2H$) to the methyl bisulfate and distilling the mixture under heating to separate and purify methyl trifluoroacetate ($CF_3CO_2CH_3$).

In first step (A), a catalyst is mixed with an acid solution and methane gas is supplied to the mixture to prepare methyl bisulfate.

The catalyst can be selected from the group consisting of Pt(0), $PtCl_2$, $PtBr_2$, $PtI_2$, Pt, $Pt(acac)_2$, $Pt(OAc)_2$, (bpym)$PtCl_2$, $(DMSO)_2PtCl_2$, NaI, KI, LiI, $CH_3I$, $CH_3CH_2I$, and $CH_3CH_2CH_2I$. The catalyst is preferably a platinum catalyst selected from the group consisting of Pt(0), $PtCl_2$, $PtBr_2$, $PtI_2$, Pt, $Pt(acac)_2$, $Pt(OAc)_2$, (bpym)$PtCl_2$, and $(DMSO)_2PtCl_2$ and is most preferably $(DMSO)_2PtCl_2$ that can be used to prepare methyl bisulfate in a 1.5 to 2 times higher yield than other catalysts.

Here, "acac", "OAc", "bpym", and "DMSO" are abbreviations for "acetylacetonate", "acetate", "2,2'-bipyrimidine", and "dimethyl sulfoxide", respectively.

The acid may be any acid that can provide an acid solution commonly used in the art but is not particularly limited thereto. The acid is a sulfur-containing acid and is preferably sulfuric acid or oleum.

The oleum refers to a solution of sulfur trioxide ($SO_3$) in sulfuric acid. The content of $SO_3$ in the oleum may vary over a wide range but is typically from 1 to 60% by weight, more preferably 20% by weight. For example, oleum containing 20% by weight of $SO_3$ indicates the presence of 20 g of $SO_3$ in 100 g of oleum.

Step (A) is preferably carried out at 150 to 250° C. A temperature lower than 150° C. results in low activity of the catalyst, leading to a low yield of methyl bisulfate. Meanwhile, a temperature higher than 250° C. causes a very rapid deactivation of the catalyst, leading to a negligible increase in yield. Step (A) is preferably carried out for 0.5 to 12 hours. A time longer than 12 hours does not increase the yield of the reaction any further.

In step (A), the catalyst is preferably added in such an amount that its concentration in the oleum is from 0.01 M to 1 M.

In next step (B), trifluoroacetic acid ($CF_3CO_2H$) is added to the methyl bisulfate and is distilled under heating to separate and purify methyl trifluoroacetate ($CF_3CO_2CH_3$).

Excess sulfuric acid and the catalyst as well as the methyl bisulfate are present in the reaction mixture obtained in step (A). The methyl bisulfate may be separated from the sulfuric acid by a general distillation process under reduced pressure. In this case, excessive energy is consumed and the methyl bisulfate is converted to dimethyl sulfate via disproportionation due to the hydrogen bonding between the methyl bisulfate and the sulfuric acid. The above-mentioned conventional methods substantially fail to separate methyl bisulfate from sulfuric acid and use unseparated methyl bisulfate for methanol production. Further, sulfuric acid present as a solvent at a high concentration is diluted to a lower concentration with excess water and is then wasted. There is thus a need to develop a process for separating and purifying methyl bisulfate from sulfuric acid to obtain high-purity methanol.

The present inventors have conducted research through a large number of repeated experiments to solve the above problems, and as a result, have succeeded in converting methyl bisulfate to methyl trifluoroacetate ($CF_3CO_2CH_3$) having a lower boiling point than other materials and separating and purifying the methyl trifluoroacetate ($CF_3CO_2CH_3$) by distillation.

When the reaction reaches equilibrium after the addition of trifluoroacetic acid ($CF_3CO_2H$) to the reaction mixture including the methyl bisulfate obtained in step (A), sulfuric acid and methyl trifluoroacetate ($CF_3CO_2CH_3$) are formed (see Reaction 2). The product methyl trifluoroacetate ($CF_3CO_2CH_3$) having a boiling point of 43° C. can be readily separated from the sulfuric acid by distillation at ambient pressure and 60 to 100° C. (step (B)).

That is, step (B) is preferably carried out at 60 to 100° C. Specifically, the mixture obtained in step (B) is fed into a distillation apparatus and distilled under heating to a temperature of 60 to 100° C. such that the methyl bisulfate reacts with the trifluoroacetic acid ($CF_3CO_2H$) to give sulfuric acid and methyl trifluoroacetate ($CF_3CO_2CH_3$). Unreacted trifluoroacetic acid ($CF_3CO_2H$) having a low boiling point is distilled off and recovered.

In step (B), the reaction temperature is preferably in the range of 60 to 100° C. Within this range, the reaction can reach equilibrium within 1 hour. If the reaction temperature is lower than 60° C., a long time of 20 to 50 hours is required to complete the reaction, that is, the esterification of the trifluoroacetic acid ($CF_3CO_2H$) is too slow. Meanwhile, if the reaction temperature exceeds 100° C., a portion of the sulfuric acid is separated, indicating the need for additional separation of the sulfuric acid.

In step (B), the methyl bisulfate and the trifluoroacetic acid ($CF_3CO_2H$) may be mixed in a molar ratio of 1:1 to 1:20. When the molar ratio is from 1:7 to 1:15, the conversion of the methyl bisulfate to methyl trifluoroacetate ($CF_3CO_2CH_3$) is increased by at least 2-fold.

Acetic acid or formic acid may be used instead of the trifluoroacetic acid ($CF_3CO_2H$). However, acetic acid or formic acid tends to be degraded by the excess solvent sulfuric acid. The use of an acid having a fluoroalkyl group, such as $CF_3CF_2CO_2H$ or $CF_3CF_2CF_2CO_2H$ is uneconomical. Trifluoroacetic acid ($CF_3CO_2H$) used in the method of the present invention is stable in sulfuric acid, is not lost or degraded during processing, and is stable enough not to induce any side reactions, unlike other acids.

The methyl trifluoroacetate ($CF_3CO_2CH_3$) thus produced is a methanol precursor and has a high purity. 0 to 0.9%, preferably 0 to 0.5%, more preferably 0 to 0.1% of sulfuric acid and by-products are present in the final product. According to conventional methods for producing methanol, methyl bisulfate as a methanol precursor is not separated from sulfuric acid and by-products remain unremoved, resulting in a significant deterioration in the purity of methanol produced from methane for transport.

In contrast, according to the method of the present invention, methyl bisulfate is converted to methyl trifluoroacetate ($CF_3CO_2CH_3$) and by-products such as sulfuric acid can be removed by distillation, ensuring high purity of the methanol.

In addition, the method of the present invention enables the production of high-purity methyl trifluoroacetate ($CF_3CO_2CH_3$) without sulfuric acid and by-products. The high-purity methyl trifluoroacetate ($CF_3CO_2CH_3$) can be used to produce high-purity methanol from methane without losing its purity.

Conventional methods for stable transport of gaseous methane have the serious problem that the purity of methane is greatly reduced due to an increased content of impurities such as sulfuric acid. In contrast, the method of the present invention can provide high-purity methyl trifluoroacetate ($CF_3CO_2CH_3$) as a methanol precursor without impurities such as sulfuric acid and has a great advantage in that the methanol precursor can be used to effectively obtain methanol or a methyl ester in high purity.

A further aspect of the present invention is directed to a method for producing methanol, including (A) mixing a catalyst with an acid solution and supplying methane gas to the mixture to prepare methyl bisulfate, (B) adding trifluoroacetic acid ($CF_3CO_2H$) to the methyl bisulfate and distilling the mixture under heating to separate and purify methyl trifluoroacetate ($CF_3CO_2CH_3$), and (C) adding water to the methyl trifluoroacetate ($CF_3CO_2CH_3$) to produce methanol.

In first step (A), a catalyst is mixed with an acid solution and methane gas is supplied to the mixture to prepare methyl bisulfate.

The catalyst can be selected from the group consisting of Pt(0), $PtCl_2$, $PtBr_2$, $PtI_2$, Pt, Pt(acac)$_2$, Pt(OAc)$_2$, (bpym)$PtCl_2$, $(DMSO)_2PtCl_2$, NaI, KI, LiI, $CH_3I$, $CH_3CH_2I$, and $CH_3CH_2CH_2I$. The catalyst is preferably a platinum catalyst selected from the group consisting of Pt(0), $PtCl_2$, $PtBr_2$, $PtI_2$, Pt, Pt(acac)$_2$, Pt(OAc)$_2$, (bpym)$PtCl_2$, and $(DMSO)_2PtCl_2$ and is most preferably $(DMSO)_2PtCl_2$ that can be used to prepare methyl bisulfate in a 1.5 to 2 times higher yield than other catalysts.

Here, "acac", "OAc", "bpym", and "DMSO" are abbreviations for "acetylacetonate", "acetate", "2,2'-bipyrimidine", and "dimethyl sulfoxide", respectively.

The acid may be any acid that can provide an acid solution commonly used in the art but is not particularly limited thereto. The acid is preferably sulfuric acid or oleum.

The oleum refers to a solution of sulfur trioxide ($SO_3$) in sulfuric acid. The content of $SO_3$ in the oleum may vary over a wide range but is typically from 1 to 60% by weight, more preferably 20% by weight. For example, oleum containing 20% by weight of $SO_3$ indicates the presence of 20 g of $SO_3$ in 100 g of oleum.

Step (A) is preferably carried out at 150 to 250° C. A temperature lower than 150° C. results in low activity of the catalyst, leading to a low yield of methyl bisulfate. Meanwhile, a temperature higher than 250° C. causes a very rapidly deactivation of the catalyst, leading to a negligible increase in yield. Step (A) is preferably carried out for 0.5 to 12 hours. A time longer than 12 hours does not increase the yield of the reaction any further.

In step (A), the catalyst is preferably added in such an amount that its concentration in the oleum is from 0.01 M to 1 M.

In next step (B), trifluoroacetic acid ($CF_3CO_2H$) is added to the methyl bisulfate and is distilled under heating to separate and purify methyl trifluoroacetate ($CF_3CO_2CH_3$).

Excess sulfuric acid and the catalyst as well as the methyl bisulfate are present in the reaction mixture obtained in step (A). The methyl bisulfate may be separated from the sulfuric acid by a general distillation process under reduced pressure. In this case, excessive energy is consumed and the methyl bisulfate is converted to dimethyl sulfate via disproportionation due to the hydrogen bonding between the methyl bisulfate and the sulfuric acid. The above-mentioned conventional methods substantially fail to separate methyl bisulfate from sulfuric acid and use unseparated methyl bisulfate for methanol production. Further, sulfuric acid present as a solvent at a high concentration is diluted to a lower concentration with excess water and is then wasted. There is thus a need to develop a process for separating and purifying methyl bisulfate from sulfuric acid to obtain high-purity methanol.

The present inventors have conducted research through a large number of repeated experiments to solve the above problems, and as a result, have succeeded in converting methyl bisulfate to methyl trifluoroacetate ($CF_3CO_2CH_3$) having a lower boiling point than other materials and separating and purifying the methyl trifluoroacetate ($CF_3CO_2CH_3$) by distillation.

When the reaction reaches equilibrium after the addition of trifluoroacetic acid ($CF_3CO_2H$) to the reaction mixture including the methyl bisulfate obtained in step (A), sulfuric acid and methyl trifluoroacetate ($CF_3CO_2CH_3$) are formed (see Reaction 2). The product methyl trifluoroacetate ($CF_3CO_2CH_3$) having a boiling point of 43° C. can be readily separated from the sulfuric acid by distillation at ambient pressure and 60 to 100° C. (step (B)).

That is, step (B) is preferably carried out at 60 to 100° C. Specifically, the mixture obtained in step (B) is fed into a distillation apparatus and distilled under heating to a temperature of 60 to 100° C. such that the methyl bisulfate reacts with the trifluoroacetic acid ($CF_3CO_2H$) to give sulfuric acid and methyl trifluoroacetate ($CF_3CO_2CH_3$). Unreacted trifluoroacetic acid ($CF_3CO_2H$) having a low boiling point is distilled off and recovered.

In step (B), the reaction temperature is preferably in the range of 60 to 100° C. Within this range, the reaction can reach equilibrium within 1 hour. If the reaction temperature is lower than 60° C., a long time of 20 to 50 hours is required to complete the reaction, that is, the esterification of the trifluoroacetic acid ($CF_3CO_2H$) is too slow. Meanwhile, if the reaction temperature exceeds 100° C., a portion of the sulfuric acid is separated, indicating the need for additional separation of the sulfuric acid.

In step (B), the methyl bisulfate and the trifluoroacetic acid ($CF_3CO_2H$) may be mixed in a molar ratio of 1:1 to 1:20. When the molar ratio is from 1:7 to 1:15, the conversion of the methyl bisulfate to methyl trifluoroacetate ($CF_3CO_2CH_3$) is increased by at least 2-fold.

Acetic acid or formic acid may be used instead of the trifluoroacetic acid ($CF_3CO_2H$). However, acetic acid or formic acid tends to be degraded by the excess solvent sulfuric acid. The use of an acid having a fluoroalkyl group, such as $CF_3CF_2CO_2H$ or $CF_3CF_2CF_2CO_2H$ is uneconomical. Trifluoroacetic acid ($CF_3CO_2H$) used in the method of the present invention is stable in sulfuric acid, is not lost or degraded during processing, and is stable enough not to induce any side reactions, unlike other acids.

In final step (C), water is added to the methyl trifluoroacetate ($CF_3CO_2CH_3$) to produce methanol. The use of the high-purity methyl trifluoroacetate ($CF_3CO_2CH_3$) collected in step (B) ensures the production of high-purity methanol without the need for further processing and enables the production of a large amount of methanol in high purity in a continuous process, as shown in FIG. 1.

Step (C) can be carried out in the range of room temperature to 100° C. Outside this range, additional energy may be consumed without a significant increase in yield.

According to the method of the present invention, the addition of the trifluoroacetic acid as a solvent capable of transesterification with the intermediate methyl bisulfate ensures relatively easy separation of the methanol precursor from sulfuric acid, enabling the production of high-purity methanol in a continuous manner in the subsequent step. Therefore, the method of the present invention can overcome the difficulties in separating and purifying the intermediate methyl bisulfate from sulfuric acid which are encountered in conventional methods for producing methanol using a platinum or iodine catalyst.

In the method for producing methanol, the high-purity methyl trifluoroacetate ($CF_3CO_2CH_3$) prepared through a series of steps (A) and (B) undergoes hydrolysis upon reaction with water to produce high-purity methanol. Alternatively, the high-purity methyl trifluoroacetate ($CF_3CO_2CH_3$) may react with a carboxylic acid represented by Formula 1:

$$R_1CO_2H \qquad (1)$$

wherein $R_1$ is selected from $C_1$-$C_{10}$ alkyl groups, to produce a methyl ester represented by Formula 2:

$$R_1CO_2CH_3 \qquad (2)$$

wherein $R_1$ is as defined in Formula 1.

By-produced trifluoroacetic acid ($CF_3CO_2H$) can be collected and recycled, as shown in FIG. 1. In this way, various types of methyl esters can be produced from methane as a raw material.

Another aspect of the present invention is directed to a method for producing a methyl ester, including (a) mixing a catalyst with an acid solution and supplying methane gas to the mixture to prepare methyl bisulfate, (b) adding trifluoroacetic acid ($CF_3CO_2H$) to the methyl bisulfate and distilling the mixture under heating to separate and purify methyl trifluoroacetate ($CF_3CO_2CH_3$), and (c) adding the methyl trifluoroacetate ($CF_3CO_2CH_3$) with a carboxylic acid represented by Formula 1:

$$R_1CO_2H \qquad (1)$$

wherein $R_1$ is selected from $C_1$-$C_{10}$ alkyl groups, to produce a methyl ester represented by Formula 2:

$$R_1CO_2CH_3 \qquad (2)$$

wherein $R_1$ is as defined in Formula 1.

In first step (a), a catalyst is mixed with an acid solution and methane gas is supplied to the mixture to prepare methyl bisulfate.

The catalyst can be selected from the group consisting of Pt(0), $PtCl_2$, $PtBr_2$, $PtI_2$, Pt, $Pt(acac)_2$, $Pt(OAc)_2$, (bpym)$PtCl_2$, $(DMSO)_2PtCl_2$, NaI, KI, LiI, MeI, EtI, and propyl iodide. The catalyst is preferably a platinum catalyst selected from the group consisting of Pt(0), $PtCl_2$, $PtBr_2$, $Pa_2$, Pt, $Pt(acac)_2$, $Pt(OAc)_2$, (bpym)$PtCl_2$, and $(DMSO)_2PtCl_2$ and is most preferably $(DMSO)_2PtCl_2$ that can be used to prepare methyl bisulfate in a 1.5 to 2 times higher yield than other catalysts.

The acid may be any acid that can provide an acid solution commonly used in the art but is not particularly limited thereto. The acid is preferably sulfuric acid or oleum.

The oleum refers to a solution of sulfur trioxide ($SO_3$) in sulfuric acid. The content of $SO_3$ in the oleum may vary over a wide range but is typically from 1 to 60% by weight, more preferably 20% by weight. For example, oleum containing 20% by weight of $SO_3$ indicates the presence of 20 g of $SO_3$ in 100 g of oleum.

The amount of the sulfuric acid used is not limited in the method of the present invention because methyl trifluoroacetate ($CF_3CO_2CH_3$) converted from methyl bisulfate can be sufficiently separated and purified by distillation even when excess sulfuric acid remains unreacted, unlike in other methods for methanol production. Therefore, the method of the present invention is easy to control regardless of the sulfuric acid concentration.

Step (a) is preferably carried out in the range of 150 to 250° C. Outside this range, methyl bisulfate is not efficiently prepared. Step (a) is preferably carried out for 0.5 to 12 hours. A time longer than 12 hours does not increase the yield of the reaction any further, which is inefficient and uneconomical.

In step (a), the catalyst is preferably added in such an amount that its concentration in the oleum is from 0.01 M to 1 M.

In next step (b), trifluoroacetic acid ($CF_3CO_2H$) is added to the methyl bisulfate and is distilled under heating to separate and purify methyl trifluoroacetate ($CF_3CO_2CH_3$).

Excess sulfuric acid and the catalyst as well as the methyl bisulfate are present in the reaction mixture obtained in step (a). The hydrogen bonding between the methyl bisulfate and the sulfuric acid makes it difficult to separate them. The above-mentioned conventional methods substantially fail to separate methyl bisulfate from sulfuric acid and use unseparated methyl bisulfate for methanol production, leading to a low yield of methanol. Further, the methyl bisulfate may be separated from sulfuric acid by forcible distillation. In this case, however, the methyl bisulfate tends to be converted to dimethyl sulfate by disproportionation. There is thus a need to develop a process for separating and purifying methyl bisulfate from sulfuric acid to obtain high-purity methanol.

The present inventors have conducted research through a large number of repeated experiments to solve the above problems, and as a result, have succeeded in converting methyl bisulfate to methyl trifluoroacetate ($CF_3CO_2CH_3$) having a lower boiling point than other materials and separating and purifying the methyl trifluoroacetate ($CF_3CO_2CH_3$) by distillation.

When the reaction reaches equilibrium after the addition of trifluoroacetic acid ($CF_3CO_2H$) to the reaction mixture including the methyl bisulfate obtained in step (a), sulfuric acid and methyl trifluoroacetate ($CF_3CO_2CH_3$) are formed (see Reaction 2). The product methyl trifluoroacetate ($CF_3CO_2CH_3$) having a boiling point of 43° C. can be readily separated from the sulfuric acid by distillation.

Step (b) is preferably carried out at 60 to 100° C. Specifically, the mixture obtained in step (b) is fed into a distillation apparatus and distilled under heating to a temperature of 60 to 100° C. such that the methyl bisulfate reacts with the trifluoroacetic acid ($CF_3CO_2H$) to give sulfuric acid and methyl trifluoroacetate ($CF_3CO_2CH_3$). Unreacted trifluoroacetic acid ($CF_3CO_2H$) having a low boiling point is distilled off and recovered.

If the reaction temperature is lower than 60, the esterification of the trifluoroacetic acid ($CF_3CO_2H$) is too slow. Meanwhile, if the reaction temperature exceeds 100° C., a portion of the sulfuric acid is separated, indicating the need for additional separation of the sulfuric acid.

In step (b), the methyl bisulfate and the trifluoroacetic acid ($CF_3CO_2H$) may be mixed in a molar ratio of 1:1 to 1:20. When the molar ratio is from 1:7 to 1:15, the conversion of the methyl bisulfate to methyl trifluoroacetate ($CF_3CO_2CH_3$) is increased by at least 2-fold.

Acetic acid or formic acid may be used instead of the trifluoroacetic acid ($CF_3CO_2H$). However, acetic acid or formic acid tends to be degraded by the excess solvent sulfuric acid. The use of an acid having a fluoroalkyl group, such as $CF_3CF_2CO_2H$ or $CF_3CF_2CF_2CO_2H$ is uneconomical. Trifluoroacetic acid ($CF_3CO_2H$) used in the method of the present invention is stable in sulfuric acid, is not lost or degraded during processing, and is stable enough not to induce any side reactions, unlike other acids.

In final step (c), the methyl trifluoroacetate ($CF_3CO_2CH_3$) is added with a carboxylic acid represented by Formula 1:

$$R_1CO_2H \qquad (1)$$

wherein $R_1$ is selected from $C_1$-$C_{10}$ alkyl groups, to produce a methyl ester represented by Formula 2:

$$R_1CO_2CH_3 \qquad (2)$$

wherein $R_1$ is as defined in Formula 1.

The present invention will be explained in more detail with reference to the following examples. However, these examples are not to be construed as limiting or restricting the scope and disclosure of the invention. It is to be understood that based on the teachings of the present invention including the following examples, those skilled in the art can readily practice other embodiments of the present invention whose experimental results are not explicitly presented. Such modifications and variations are intended to come within the scope of the appended claims.

Example 1. Separation and Purification of Methanol Precursor

1. Production of Methyl Bisulfate 30 g of a sulfuric acid solution containing 6 g (75 mmol) of $SO_3$ was placed in a 100 ml SUS autoclave and 20 mg of $(DMSO)_2PtCl_2$ was added thereto. Then, the reactor was filled with methane supplied at a pressure of 20 bar. The reactor was heated to 180° C. The reaction was allowed to proceed at 180° C. for 3 h. After completion of the reaction, the reactor was cooled down and gaseous materials were released. The reaction mixture was taken out of the reactor and diluted with $D_2SO_4$ and its $^1$H-NMR spectrum was recorded. The $^1$H-NMR spectrum is shown in (a) of FIG. 2. Methanesulfonic acid ($CH_3SO_3H$) was used as the internal standard.

Figure 2:
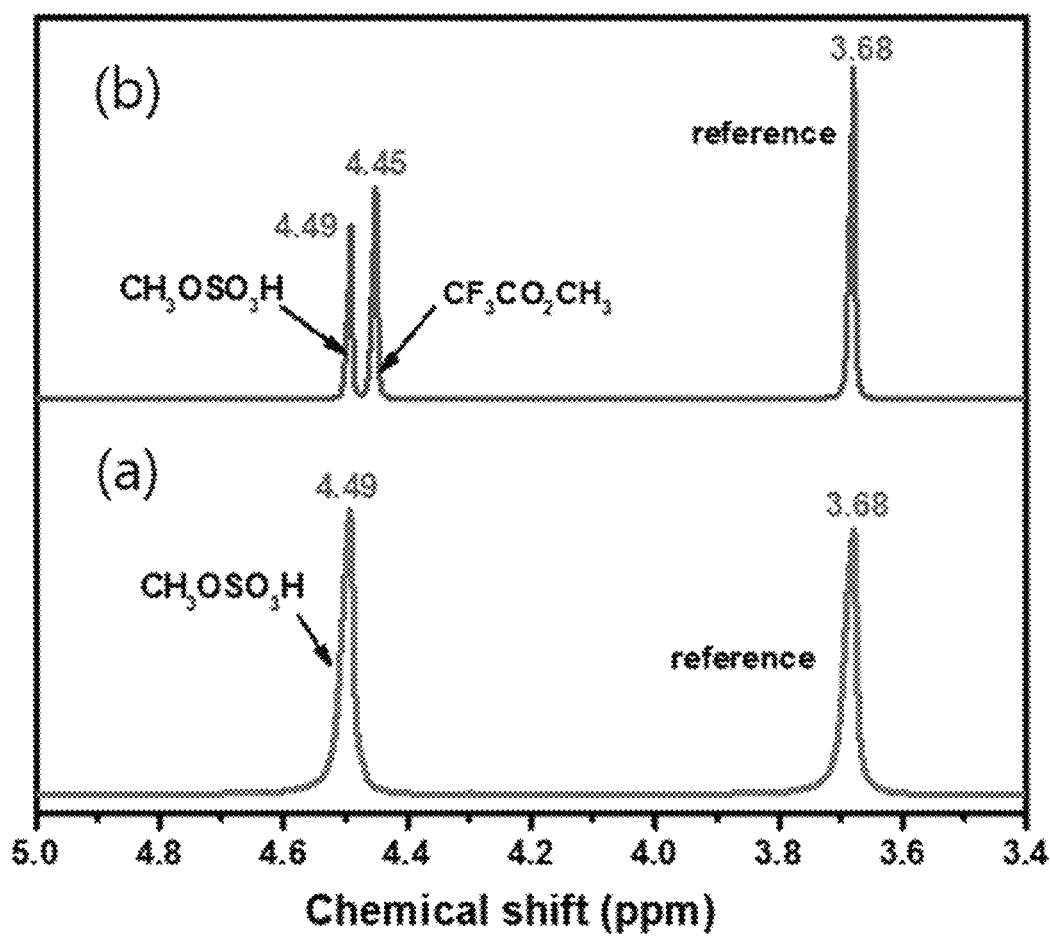
FIG. 2 shows (a) a $^1$H-NMR spectrum of a reaction mixture of oleum and methane in the presence of a catalyst (Example 1.1) and (b) a $^1$H-NMR spectrum of a reaction mixture obtained in Example 1.2, demonstrating the conversion of methyl bisulfate to methyl trifluoroacetate ($CF_3CO_2CH_3$) as depicted in Reactions 1 and 2.

The production of methyl bisulfate ($CH_3OSO_3H$, MBS) was quantified from (a) of FIG. 2. As a result of the reaction, 32.5 mmol of methyl bisulfate ($CH_3OSO_3H$) and 1.5 mmol of $CO_2$ were synthesized.

The conversion rate of methane, the production rate of the oxide, and the selectivity for the oxide were determined as follows:

Conversion rate of methane (%)=[Amount of MBS produced (mmol)+Amount of $CO_2$ produced (mmol)]×2/Amount of oxidant used (mmol)

Yield of MBS (%)=Amount of MBS produced (mmol)×2/Amount of oxidant used (mmol)

Selectivity for MBS (%)=Amount of MBS produced (mmol)/[Amount of MBS produced (mmol)+ Amount of $CO_2$ produced (mmol)]

The conversion rate of methane, the yield of methyl bisulfate (MBS), and the selectivity for methyl bisulfate (MBS) were found to be 90.6%, 87.5%, and 95.5%, respectively.

2. Production of Methyl Trifluoroacetate ($CF_3CO_2CH_3$)

Trifluoroacetic acid ($CF_3CO_2H$) was added to the reaction mixture including methyl bisulfate. The reaction of the trifluoroacetic acid ($CF_3CO_2H$) and the methyl bisulfate reached equilibrium, methyl trifluoroacetate ($CF_3CO_2CH_3$) was formed (see Reaction 2). The trifluoroacetic acid was added in an amount of 18 g (160 mmol) such that the methyl bisulfate and the trifluoroacetic acid ($CF_3CO_2H$) were mixed in a molar ratio of 1:2.49.

Since the product methyl trifluoroacetate ($CF_3CO_2CH_3$) has a boiling point of 43° C., distillation was performed under heating to 80° C. at ambient pressure to separate and purify the methyl trifluoroacetate ($CF_3CO_2CH_3$) from the reaction mixture including sulfuric acid.

Figure 4A:
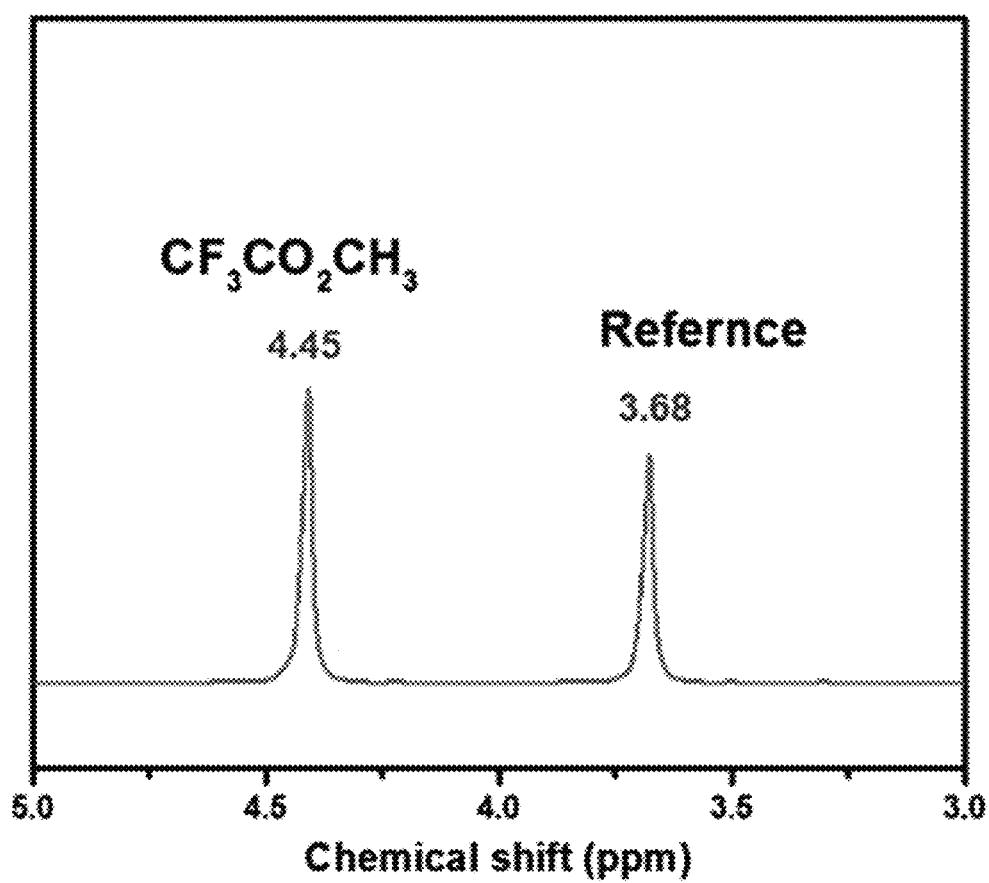
FIGS. 4A and 4B show a $^1$H-NMR spectrum and a gas chromatogram (GC) of a product collected after simple distillation of a reaction mixture obtained in Example 1, respectively.

A portion of the reaction mixture (including sulfuric acid) obtained by addition of the trifluoroacetic acid ($CF_3CO_2H$) to the methyl bisulfate was sampled and used for $^1$H-NMR analysis. The results are shown in (b) of FIG. 2. After simple distillation, the collected product was analyzed by $^1$H-NMR and GC. The results are shown in FIG. 4A. As a result, $CF_3CO_2CH_3$ and $CH_3OSO_3H$ coexisted before distillation but the collected product was found to be $CF_3CO_2CH_3$.

$$CH_3OSO_3H + CF_3CO_2H \leftrightarrow H_2SO_4 + CF_3CO_2CH_3 \quad (2)$$

Example 2. Separation and Purification of Methanol Precursor

Methyl trifluoroacetate was synthesized, separated, and purified in the same manner as in Example 1, except that the methyl bisulfate and the trifluoroacetic acid ($CF_3CO_2H$) were mixed in a molar ratio of 1:4.96.

Example 3. Separation and Purification of Methanol Precursor

Methyl trifluoroacetate was synthesized, separated, and purified in the same manner as in Example 1, except that the methyl bisulfate and the trifluoroacetic acid ($CF_3CO_2H$) were added in a molar ratio of 1:7.06.

Example 4. Methanol Synthesis

The methyl trifluoroacetate ($CF_3CO_2CH_3$) separated and purified in Example 1 was hydrolyzed by addition to water to produce methanol, as depicted in Reaction 3.

$$CF_3CO_2CH_3 + H_2O \leftrightarrow CF_3CO_2H + CH_3OH \quad (3)$$

Experimental Example 1. Measurement of Equilibrium Constants Between the Methyl Bisulfate and the Trifluoroacetic Acid The equilibrium constants between the methyl bisulfate and the trifluoroacetic acid in Examples 1-3 were measured. First, trifluoroacetic acid ($CF_3CO_2H$) solutions containing 5 wt % of $CH_3SO_3H$ as the standard were prepared, as in Examples 1-3. The concentrations of the methyl bisulfate ($CH_3OSO_3H$) and the trifluoroacetic acid ($CF_3CO_2CH_3$) in the solutions were measured by $^1$H-NMR spectroscopy.

The equilibrium constant represents the relationship between reactant and product concentrations. The concentrations of $CH_3OSO_3H$, $CF_3CO_2H$, $H_2SO_4$, and $CF_3CO_2CH_3$ in the reaction mixtures when the reaction reached equilibrium in Examples 1-3 were measured and the equilibrium constants ($K_{eq}$) at 25° C. was calculated by substituting the measured concentrations into Equation 1:

$$K_{eq} = [H_2SO_4 \text{ concentration}][CF_3CO_2CH_3 \text{ concentration}] / [CH_3OSO_3H \text{ concentration}][CF_3CO_2H \text{ concentration}] \quad (1)$$

where [$CH_3OSO_3H$ concentration] and [$CF_3CO_2H$ concentration] are the amounts of $CH_3OSO_3H$ and $CF_3CO_2H$ remaining after the reaction reached equilibrium, respectively.

[$CH_3OSO_3H$ concentration] and [$CF_3CO_2CH_3$ concentration] were measured by NMR. [$H_2SO_4$ concentration] was calculated by adding the concentration of sulfuric acid initially used to the concentration of $CF_3CO_2CH_3$ produced after equilibrium was reached. [$CF_3CO_2H$ concentration] was calculated by subtracting the concentration of $CF_3CO_2CH_3$ produced after equilibrium was reached from the concentration of $CF_3CO_2H$ initially used. The results are shown in Table 1.

TABLE 1

| | Before equilibrium | | | After equilibrium | | | | |
|---|---|---|---|---|---|---|---|---|
| No. | $H_2SO_4$ (mmol) | MBS (mmol) | $CF_3CO_2H$ (mmol) | $H_2SO_4$ (mmol) | MBS (mmol) | $CF_3CO_2H$ (mmol) | $CF_3CO_2CH_3$ (mmol) | $K_{eq}$ |
| Example 1 | 244.7 | 32.5 | 80.9 | 264.3 | 12.9 | 61.3 | 19.6 | 6.56 |
| Example 2 | 244.7 | 32.5 | 161.2 | 269.7 | 7.5 | 136.2 | 25.0 | 6.65 |
| Example 3 | 244.7 | 32.5 | 229.5 | 271.7 | 5.5 | 202.5 | 27.0 | 6.57 |

As can be seen from the results in Table 1, the equilibrium constants in Examples 1-3 were an average of 6.6 at 25° C., demonstrating that the forward reaction was favored until equilibrium was reached.

Experimental Example 2. Measurement of Times it Took to Reach Equilibrium at Different Temperatures The times it took to reach equilibrium when methyl bisulfate was mixed with trifluoroacetic acid ($CF_3CO_2H$) were measured. 0.3 g of a $CF_3CO_2H$ solution containing 0.5 wt % of $CH_3SO_3H$ as the internal standard was added to 0.5 g of a sulfuric acid solution containing methyl bisulfate (MBS) at a concentration of 2.1 M. The mixture were divided and placed in NMR tubes and the reaction was allowed to proceed at different temperatures of 25° C., 40° C., and 60° C. The amounts of the reaction product $CF_3CO_2CH_3$ in the NMR tubes were measured by NMR. The results are shown in FIG. 3.

Figure 3:
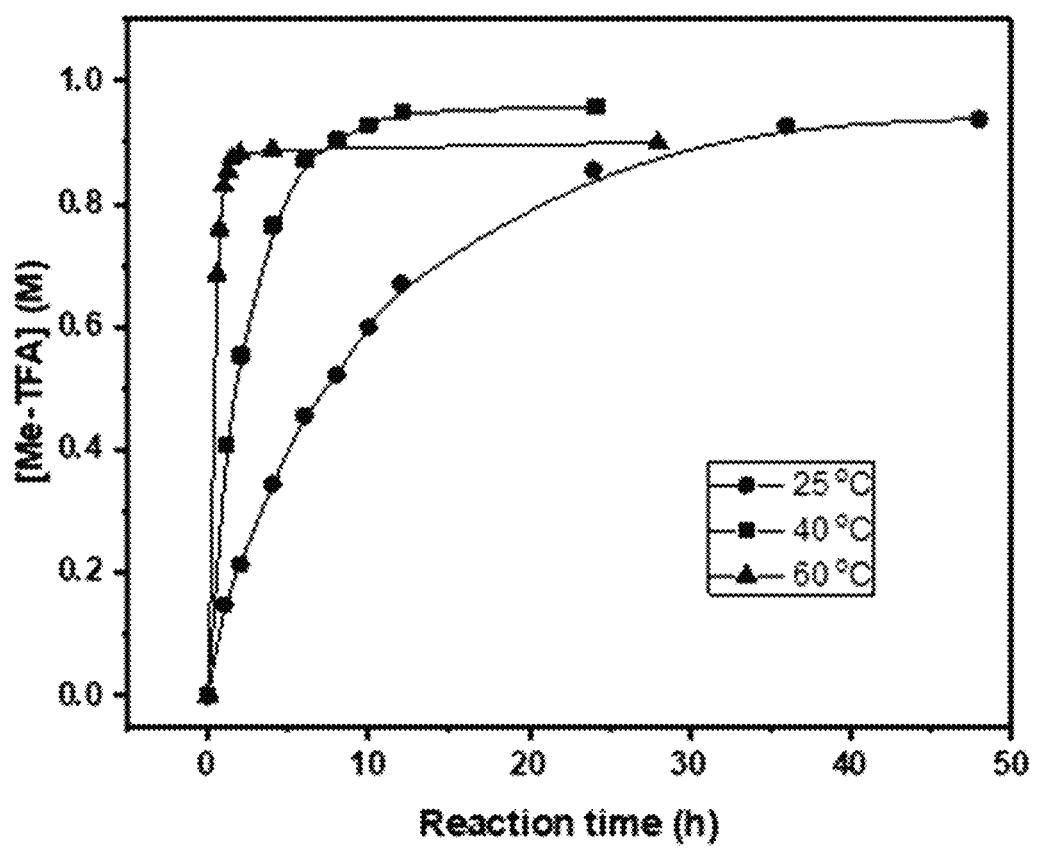
FIG. 3 shows the times it took for a reaction of methyl bisulfate and trifluoroacetic acid ($CF_3CO_2H$) to reach equilibrium at different reaction temperatures.

FIG. 3 shows the times it took for the reaction of the methyl bisulfate and the trifluoroacetic acid ($CF_3CO_2H$) to reach equilibrium at different reaction temperatures. The times it took to reach equilibrium where the $CF_3CO_2CH_3$ concentration was made constant were ≥50 h at 25° C., ≥20 h at 40° C., and 1 h at 60° C. In conclusion, it is preferable to carry out separation and purification step (B) at 60-100° C.

Experimental Example 3. Distillation Reaction

Methyl bisulfate prepared by oxidation of methane was mixed and reacted with sulfuric acid, as in Example 1. To the reaction mixture was added 18 g (160 mmol) of $CF_3CO_2H$. The reaction was allowed to proceed. The resulting reaction mixture was subjected to simple distillation at ambient pressure under heating at 80° C. The distillate was collected and analyzed by NMR and GC. The results are shown in FIGS. 4A and 4B.

Figure 4B:
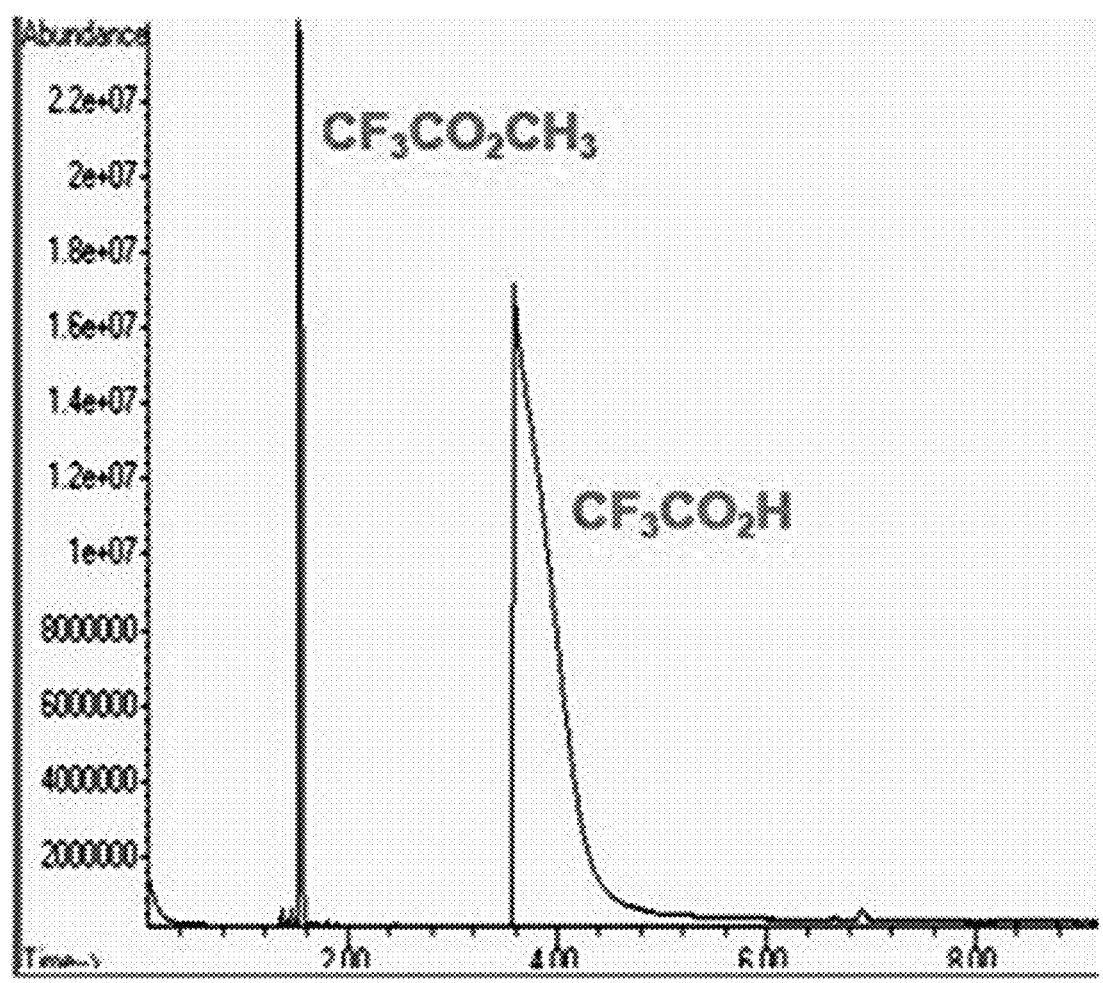

As shown in FIGS. 4A and 4B, 4 g of $CF_3CO_2CH_3$ (30.5 mmol) and 12 g (105 mmol) of $CF_3CO_2H$ only were present in the distillate collected after simple distillation. That is, it was found that only $CF_3CO_2CH_3$ was separated/purified in high purity from the reaction mixture containing sulfuric acid and many impurities after purification.

The reaction mixture remaining in the reactor was analyzed by NMR and GC. As a result, only 2 mmol of methyl bisulfate was found to be present, demonstrating that MBS was converted to $CF_3CO_2CH_3$ in a yield of 94% and $CF_3CO_2CH_3$ was separated/purified in high purity by distillation.

The $CF_3CO_2CH_3$ thus produced had a high purity and 0 to 0.9% (preferably 0 to 0.5%, more preferably 0 to 0.1%) of sulfuric acid and by-products were present therein (FIGS. 4A and 4B). Conventional methods for producing methanol fail to separate methyl bisulfate from sulfuric acid and use unseparated by-products for methanol production. In contrast, the inventive method for producing methanol has great advantages in that a solution containing high-purity $CF_3CO_2CH_3$ without sulfuric acid and by-products can be obtained and the addition of water to the solution enables the production of high-purity methanol.

Methods for converting gaseous methane to high value-added compounds (for example, methanol) by oxidation of methane with sulfuric acid are suitable for the production of desired oxides in higher yields than other methods but have limitations in separating and purifying the products (for example, methanol). In contrast, easy-to-separate and easy-to-purify $CF_3CO_2CH_3$ can be converted to methanol or a methyl ester in a simple, easy, rapid, and safe way in the subsequent step, thus being very useful for the production of methanol or a methyl ester.

Specifically, simple addition of water to high-purity $CF_3CO_2CH_3$ enables the production of high-purity methanol through hydrolysis, as depicted in Reaction 3:

$$CF_3CO_2CH_3 + H_2O \leftrightarrow CF_3CO_2H + CH_3OH \quad (3)$$

In addition, simple addition of a carboxylic acid represented by Formula 1:

$$R_1CO_2H \quad (1)$$

wherein $R_1$ is selected from $C_1$-$C_{10}$ alkyl groups, to high-purity $CF_3CO_2CH_3$ enables the production of a high-purity methyl ester represented by Formula 2:

$$R_1CO_2CH_3 \quad (2)$$

wherein $R_1$ is as defined in Formula 1.

What is claimed is:

1. A method for producing methyl trifluoroacetate having high-purity, comprising the steps of:
   (a) preparing methyl bisulfate by mixing a catalyst with an acid solution comprising a sulfur-containing acid to provide a first mixture and supplying methane gas to the first mixture to prepare the methyl bisulfate; and
   (b) preparing methyl trifluoroacetate ($CF_3CO_2CH_3$) by adding trifluoroacetic acid ($CF_3CO_2H$) to the first mixture including the methyl bisulfate to provide a second mixture and distilling the second mixture under heating to prepare, separate and purify the methyl trifluoroacetate ($CF_3CO_2CH_3$).

2. The method according to claim 1, wherein the catalyst is selected from the group consisting of $Pt^0$, $PtCl_2$, $PtBr_2$, $PtI_2$, Pt, $Pt(acac)_2$, $Pt(OAc)_2$, $(bpym)PtCl_2$, $(DMSO)_2PtCl_2$, NaI, KI, LiI, $CH_3I$, $CH_3CH_2I$, and $CH_3CH_2CH_2I$.

3. The method according to claim 1, wherein the sulfur-containing acid is sulfuric acid or oleum.

4. The method according to claim 1, wherein, in step (b), the methyl bisulfate and the trifluoroacetic acid ($CF_3CO_2H$) are mixed in a molar ratio ranging from 1:1 to 1:10.

5. The method according to claim 1, wherein step (b) is carried out at a temperature ranging from 70 to 100° C.

6. A method for producing methanol, comprising the steps of:
   (a) preparing methyl bisulfate by mixing a catalyst with an acid solution comprising a sulfur-containing acid to provide a first mixture and supplying methane gas to the first mixture to prepare the methyl bisulfate;
   (b) preparing methyl trifluoroacetate ($CF_3CO_2CH_3$) by adding trifluoroacetic acid ($CF_3CO_2H$) to the first mixture containing the methyl bisulfate to provide a second mixture and distilling the second mixture under heating to prepare, separate and purify the methyl trifluoroacetate ($CF_3CO_2CH_3$); and
   (c) preparing methanol by adding water to the methyl trifluoroacetate ($CF_3CO_2CH_3$) to produce the methanol.

7. The method according to claim 6, wherein the catalyst is selected from the group consisting of $Pt^0$, $PtCl_2$, $PtBr_2$, $PtI_2$, Pt, $Pt(acac)_2$, $Pt(OAc)_2$, $(bpym)PtCl_2$, $(DMSO)_2PtCl_2$, NaI, KI, LiI, $CH_3I$, $CH_3CH_2I$, and $CH_3CH_2CH_2I$.

8. The method according to claim 6, wherein the sulfur-containing acid is sulfuric acid or oleum.

9. The method according to claim 6, wherein in step (b), the methyl bisulfate and the trifluoroacetic acid ($CF_3CO_2H$) are mixed in a molar ratio of 1:1 to 1:10.

10. The method according to claim 1, wherein step (b) is carried out at a temperature ranging from 70 to 100° C.

11. A method for producing a methyl ester, comprising the steps of:
   (a) preparing methyl bisulfate by mixing a catalyst with an acid solution comprising a sulfur-containing acid to provide a first mixture and supplying methane gas to the first mixture to prepare the methyl bisulfate;
   (b) preparing methyl trifluoroacetate ($CF_3CO_2CH_3$) by adding trifluoroacetic acid ($CF_3CO_2H$) to the first mixture including the methyl bisulfate to provide a second mixture and distilling the second mixture under heating to prepare, separate and purify the methyl trifluoroacetate ($CF_3CO_2CH_3$); and
   (c) preparing a methyl ester represented by Formula 2 below by adding a carboxylic acid represented by Formula 1 below to the methyl trifluoroacetate ($CF_3CO_2CH_3$):

$$R_1CO_2H \quad (1),$$

where $R_1$ is selected from $C_1$-$C_{10}$ alkyl groups, $$R_1CO_2CH_3 \quad (2),$$

where $R_1$ is as defined in Formula 1.

12. The method according to claim 11, wherein the catalyst is selected from the group consisting of $Pt^0$, $PtCl_2$, $PtBr_2$, $PtI_2$, Pt, $Pt(acac)_2$, $Pt(OAc)_2$, $(bpym)PtCl_2$, $(DMSO)_2PtCl_2$, NaI, KI, LiI, $CH_3I$, $CH_3CH_2I$, and $CH_3CH_2CH_2I$.

13. The method according to claim 11, wherein the sulfur-containing acid is sulfuric acid or oleum.

14. The method according to claim 11, wherein, in step (b), the methyl bisulfate and the trifluoroacetic acid ($CF_3CO_2H$) are mixed in a molar ratio ranging from 1:1 to 1:10.

15. The method according to claim 11, wherein step (B) is carried out at a temperature ranging from 70 to 100° C.

* * * * *